United States Patent
Sheridan

(10) Patent No.: US 6,559,353 B1
(45) Date of Patent: May 6, 2003

(54) TREATED DISPOSABLE ARTICLES FOR REDUCING SKIN BREAKDOWN

(76) Inventor: Christopher H. Sheridan, 114-14 St., Cress Kill, NJ (US) 07626

(*) Notice: Subject to any disclaimer, the term of this patent is extended or adjusted under 35 U.S.C. 154(b) by 0 days.

(21) Appl. No.: 08/374,907

(22) Filed: Jan. 19, 1995

(51) Int. Cl.$^7$ .................................................. A61F 13/15
(52) U.S. Cl. .......................... 604/367; 604/367; 252/91; 428/288
(58) Field of Search ................................ 604/367, 368, 604/369; 252/91; 428/288, 289, 290; 424/445; 525/384

(56) References Cited

U.S. PATENT DOCUMENTS

| | | | |
|---|---|---|---|
| 3,912,665 A | * 10/1975 | Spitzer et al. | 604/289 |
| 4,263,363 A | * 4/1981 | Buck et al. | 604/369 |
| RE31,822 E | * 2/1985 | Erickson et al. | 604/369 |
| 4,500,585 A | * 2/1985 | Erickson | 604/367 |
| 4,753,844 A | * 6/1988 | Jones et al. | 428/288 |
| 4,904,524 A | * 2/1990 | Yoh | 428/311.3 |
| 4,946,617 A | * 8/1990 | Sheridan et al. | 252/91 |
| 5,064,653 A | * 11/1991 | Sessions et al. | 424/445 |
| 5,091,102 A | * 2/1992 | Sheridan | 252/91 |
| 5,141,803 A | * 8/1992 | Pregozen | 428/288 |
| 5,164,459 A | * 11/1992 | Kimura et al. | 525/384 |
| 5,300,286 A | * 4/1994 | Gee | 424/78.03 |

* cited by examiner

Primary Examiner—John G. Weiss
Assistant Examiner—Jacqueline F Stephens

(57) ABSTRACT

A disposable waste containment composite is disclosed for fabrication into baby diapers, incontinent briefs, feminine hygiene pads, incontinent under pads and sheets, wound dressings and the like. The composite is formed from a liquid permeable topsheet, an absorbent core and an impermeable backing sheet unified by the use of adhesives, heat and pressure, ultra sonic welding and the like. The composite is characterized in that its topsheet has been treated with a non-aqueous composition comprising propylene glycol, a non-water soluble protectant, and a surface active agent. The treatment composition can also preferably include an emollient an anti-odorant, a healing agent or the like. A unique feature of the treatment is that the non-water soluble components do not restrict or interfere with the passage of bodily waste into the absorbent core. The top sheet so treated delivers in use the protectant and other agents such as the healing agent, to the surface of the skin so that when the fabricated article is employed, the incidence of contact dermatitis, skin irritations, maceration and pressure ulcers are reduced. In addition, the use of this unique topsheet treatment reduces friction which, along with the other benefits, can virtually eliminate the need for separately using medicated creams, ointments or powders.

22 Claims, No Drawings

TREATED DISPOSABLE ARTICLES FOR REDUCING SKIN BREAKDOWN

The present invention relates to treated disposable absorbent articles such as diapers, incontinent briefs, incontinent pads, bandages, dressings and the like which are effective in preventing or reducing diaper rash (contact irritant dermatitis) particularly in infants and the occurrence of bed sores and ulcerations in non-ambulatory, incontinent subjects. More particularly, the invention relates to the dry treated cover sheet useful in the fabrication of such articles.

Existing absorbent articles such as diapers, incontinent briefs, feminine hygiene pads and incontinent under pads conventionally include a topsheet or cover sheet. The topsheet is that part of the absorbent article which is in direct contact with the skin of the user. Chemical treatment of these topsheets has heretofore been limited to the addition of surface active agents to facilitate the transfer of liquid waste through the topsheet and into an absorbent core. To date, attempts to incorporate skin softeners and protectants, and/or friction reducing emollients into the topsheet has resulted in the repelling of the body fluids, rendering the absorbent articles non-functional for their intended purpose.

One object of the invention is to apply skin softeners, protectants and friction reducing emollients to a topsheet in a manner that will be effective to transfer these softeners, protectants and emollients to the skin by contact, without affecting the functionality of the absorbent article.

In U.S. Pat. No. 5,091,102 issued to the inventor herein there is disclosed a method of making a substantially flexible dry matrix using no water other than that naturally present in the matrix by utilizing non-aqueous treatment solutions comprising cationic surfactants. The patent additionally discloses incorporating propylene glycol and anti-microbial compounds in the non-aqueous treatment solutions.

The substantially dry matrices prepared according to that patent are composed only of water soluble chemicals and compounds. The addition of water or an aqueous liquid is required in order to solubilize the treatment compounds and render the articles functional.

In applicant's co-pending application, Ser. No. 08/171,676 filed Dec. 22, 1993, there is disclosed the addition of nonwater soluble compounds such as mineral oil, silicones and the like to the non-aqueous treatment solution. When water or other aqueous liquid is added to the substantially dry treated matrices, an "instant emulsion" is created which transfers the non-water soluble compound to the surface that the matrix contacts in use.

The instant application is directed to a substantially dry matrix which has been treated with a non-aqueous treatment solution comprising non-water soluble skin softening protectant and emollient compounds, non-ionic and cationic surfactants, humectants preferably propylene glycol, and preferably an anti-microbial compound.

The treated article containing the non-aqueous treatment solution, is capable of transferring the skin softening protectant and emollient compounds to the skin by contact while allowing the treated article to transfer bodily fluids through the treated topsheet and into the absorbent core.

The absorbent articles, of the invention, comprise (a) a liquid impervious backing sheet; (b) a flexible absorbent core positioned between the backing sheet and the topsheet and (c) a relatively hydrophobic, liquid pervious topsheet positioned on top of the flexible absorbent core, which effects direct skin contact. More specifically, the present invention is directed to the unique topsheet treatment for these absorptive articles which will allow the discharged body waste to pass into the absorptive layer (core) and at the same time transfer to the exposed skin in contact with the absorptive device, pharmacologic agent(s) that on delivery to the skin will function (a) to protect the subject's skin from wetness contained in the moisture absorbent layer and thus help prevent or reduce excessive hydration and skin irritation; (b) to have activity which will serve to reduce the ammonia producing organisms or enzymes which can aggravate contact irritation; (c) to reduce the odors due to waste decomposition in an occlusive anaerobic environment; and (d) in the of case of adult, particularly non-ambulatory, incontinent underpads, briefs and liners, to help reduce the skin maceration, pressure ulcers and bed sores that otherwise frequently occur by preventing skin friction and shearing and their damaging effects on the skin. The uniquely treated topsheet of the invention can also substantially reduce or eliminate the need for using creams, ointments or powders.

BACKGROUND OF THE INVENTION

Diaper dermatitis is the most common cutaneous disorder of infancy and early childhood, however this condition is not limited to infants. Any individual who suffers from incontinence may develop this condition; this ranges from newborns to the elderly, to the critically ill and/or non-ambulatory individuals.

In the case of elderly, non-ambulatory and incontinent individuals, diaper dermatitis is simply the primary irritant becoming a variable symptom complex, incorporating a combination of irritating factors, including pressure, friction, shearing, heat, moisture and the physiological effects of ageing on the body. Although frequently no more than a disagreeable nuisance, with infants and babies, this chain of events in elderly individuals can cause eruptions which progress to secondary infection and ulceration and become complicated by other disorders which can and are life threatening.

For years, ammonia produced by bacterial breakdown of urea in the urine was thought to be a major factor in the etiology of diaper rash. Some recent studies refute the role of ammonia and urea-splitting bacteria as the underlying cause of this disorder and incriminate instead a combination of wetness, impervious diaper coverings and fungi, such as Candida albicans as causative factors in the initiation of diaper rash eruptions and skin ulceration.

Investigators now believe the activity of proteolytic and lipolytic fecal enzymes present in a mixture of feces and urine to be a major factor in producing skin irritation. Urine in contact with the fecal enzymes can result in production of ammonia which raises skin pH to levels of 6.0 and above, increasing the fecal proteolytic and lipolytic enzymatic activity which in turn produces metabolites resulting in diaper rash. Urine itself contributes to diaper dermatitis by adding moisture to the diaper environment, diminishing the barrier property of the skin, thereby enhancing the skin's susceptibility to irritation of all types, including that caused by the decomposing urine and fecal metabolic products.

The occlusive nature of the diaper or incontinence brief contributes to the excess hydration of the exposed skin and to the loss of the normal barrier functions resulting in the increased vulnerability of the skin to toxic chemicals and microbial stimuli as well as to infection from fungal and other microbial organisms. Hydration and loss of the skin's normal barrier function is aggravated, particularly if left in an occluded environment for long periods of time. These results can occur with either baby diapers or with adult incontinent briefs and underpads, where, due to thinner and less healthy epidermal tissue the resulting ulcerations can become life threatening. Conservative management, in preventing and reducing diaper dermatitis and pressure ulcers is directed at keeping the skin clean and dry and by limiting irritation and maceration by the judicious use of disposable garments designed to help prevent such conditions. Most important is the prevention of irritation as a consequence of frictional shear on the skin particularly in non-ambulatory adults especially the elderly and incontinent adult.

Incontinent articles are known for containment of urine and feces. These are formed from three basic structural elements: (a) a liquid impervious backing sheet, (b) an absorbent core which may comprise one or more distinct layers or zones and, (c) a relatively hydrophobic, liquid pervious topsheet.

In addition there has been proposed the use of an insert which contains agent(s) having a buffering action or specific friction reducing action. Such an insert could be placed on top of the topsheet next to the skin of the wearer or between any of the three layers or even in a pouch or pocket formed from the liquid pervious topsheet and the liquid impervious bottom sheet. These inserts, with their friction reducing emollients however, effectively impede the passage of bodily fluids into the absorptive core and thus render their use with incontinent articles to be counterproductive by displacing one problem for another.

The topsheet, of the present invention as now proposed differs from the topsheets heretofore available in that it can be prepared so as to incorporate therein friction reducing emollients, skin protectants, and wound healing agents and/or anti-odorants, without encumbering or reducing the topsheet's ability to facilitate the passage of liquids to the absorptive core.

The topsheet which is intended for use in fabricating the articles described herein can be made in part or completely of synthetic fibers or films from such materials as polyester, modified polyolefins such as low density polyethylene and polypropylene, modified polyesters and modified poly (acrylonitriles). Examples of materials of these types include oxidized cellulosics, phosphorylated cellulosics, carboxymethylated cellulosics, grafts of cellulosics with polyacrylics, sulfonated polyolefins, partially hydrolyzed poly (acrylonitriles) and partially hydrolyzed polyesters or the like. The topsheet can also be made of natural fibers, modified celluloses such as cotton, ramie and the like. In non-woven topsheets, the fibers are bound together by a thermal bonding procedure or by polymeric binders such as polyacrylates. This sheet is substantially porous and encourages liquid materials to readily pass through into the underlying absorbent core.

A suitable type of topsheet, is for example, formed from a liquid impervious polymeric material such as a polyolefin. Such topsheets can have tapered capillaries to permit flow of discharged liquid materials through the topsheet into the underlying absorbent core.

The absorbent core is positioned between the backing sheet and the topsheet. Such an absorbent core essentially comprises a web or batt of hydrophilic fiber material. Examples of hydrophilic fiber material include, cellulose, modified cellulose, rayon, polyesters such as polyethyleneterephthalat (Dacron). The core of the absorbent layer often includes discrete particles of hydrogel materials. Such hydrogel materials are inorganic or organic compounds capable of absorbing fluids and retaining them under moderate pressures. The hydrogels can be silica gels or organic compounds such as cross-linked polymers. Examples of polymeric materials include the polyacrylamides, polyvinyl alcohol, ethylene maleic anhydride copolymers, polyvinyl ethers, hydroxypropyl cellulose, carboxymethyl cellulose etc.

The bottom sheet is constructed from a thin, plastic film of polyethylene, polypropylene or other flexible moisture impeding material which is substantially water or liquid impervious.

Urine and/or fecal containing garments and pads have previously been designed and modified to overcome some of the inherent problems associated with their use. Problems of size, weight, absorbency, and containment of odors as well as aesthetics and cost seem to be controllable. The problems of diaper dermatitis, bed sores and ulcers and their associated skin maceration, irritation and infection are still not solved. This becomes quite obvious when one realizes that diaper dermatitis is still the most common cutaneous childhood disorder and a very serious problem in the elderly and non-ambulatory incontinent individual as evidenced by the incidence of bed sores and ulcers and their tendency to become secondarily infected. The difficulty in treating these ulcers and bed sores is well known.

Efforts to reduce the incidence of diaper dermatitis, macerated skin, bed sores and ulcers include, for example, attempts to prevent a rise in skin pH to alkaline levels. The attempts for maintaining appropriate pH involve taking steps to inhibit ammonia production in the discharged wastes in the containment garment or pads by including materials that donate protons to the discharged liquids held within the absorbent article, or by a combination of known methods. One type of pH control agent or "buffering agent" frequently found in disposable absorbent articles comprises the slightly cross-linked polymeric gelling agents or "superabsorbents" which serve to imbibe liquids discharged into the article. These materials frequently contain at least some unneutralized carboxylic and/or sulfonic acid groups in the polymer chain and these acid groups can donate protons to the fluid held within the containment garment. This type of control does not function well in the presence of high ammonia concentration, i.e., elevated pH after discharge of body fluids and after the garment has been in use for a while. Another system to control both odor and pH utilizes an acidic buffering agent component and in addition incorporates a nontoxic, nonirritating, nonvolatile antimicrobial agent into the garment.

The hydrophobic, liquid pervious topsheet can also be made so that it contains acidic functional moieties in the structure of the polymers forming the topsheet. These acid moieties impart an ionexchange capacity to the topsheet and can, upon exposure to body wastes, release protons in an amount effective to lower or adjust the skin pH.

These improvements and advantages which are realized in accordance with the invention are realized by applying to the topsheet of the composite construction formed of a relatively highly liquid pervious topsheet made from a fabric or film material, a treatment solution having incorporated therein such pharmacologic agents as will not interfere with transfer of fluids through the topsheet into the absorbent core but which however can be transferred from the topsheet to the skin to exert action as protectants, healing agents, anti-fungals, buffers and anti-irritants.

In accordance with the invention, the topsheet is treated with a treatment composition comprising a glycol, a surfactant, and skin protectant. Optionally, there is also present an emollient, an anti-fungal, an anti- microbial and an/or odor reducing agent. The glycol is preferably propylene glycol, and is present in an amount of 5–75% of the composition, preferably 10–55% and is USP grade. The protectants are present in an amount of 5–50% of the total composition and preferably 20–40%. The surfactants are present in an amount of 0.5–30% of the composition and preferably 10–30%. The emollients are present in an amount of 0–60%, preferably 20–40%.

The treatment composition is applied to the topsheet in an amount of from 5–50 weight percent, preferably 5–25 weight percent and most preferably 10–20 weight percent referred to the topsheet.

The above treatment composition is entirely nonaqueous i.e., no water has been added in formulating the same. It is applied by spraying, printing, as with a Gravure press, impregnating or by other conventional methods.

Preferably the treatment composition includes an antimicrobial and/or odor reducing agent. The latter components are present in amounts depending on the specific component utilized, said amounts being well known to those skilled in the art.

More particularly the treatment compositions of the invention include:

(1) Skin Protectants. Suitable skin protectants include absorbents which remove urine from the skin, or absorbents which bind, hold and neutralize urine and other irritating and toxic substances such as ammonia. Also useful herein are skin protectants which form a physical barrier. These also soothe and soften the skin and may additionally lubricate thereby preventing chaffing. Skin protectants can be used on uninjured skin to prevent the occurrence of pathology, or if the skin is only mildly irritated, skin protectants may relieve the rash, maceration, and excessive hydration. The skin protectants have a variety of properties peculiar to themselves. They can be aborbents, lubricants, act as barriers, they soften as well as protect the skin from dryness and other harmful agents and act to impart low friction between the composite structure and the adjacent areas of the subject. They provide a smooth feel or hand which also aids in and prevents the occurrence of friction between the article, for example, bed pad and-the overlaying skin. This is particularly true in areas of high pressure as for example bony protuberance areas. These substances tend to be physically soothing, and chemically inactive, so they are safe for regular use. Such treated garments, diapers or pads may be applied routinely. Protective agents approved by the FDA as safe and effective for the prevention and treatment of diaper dermatitis include allantoin, calamine, cod liver oil, silicone, kaolin, lanolin, mineral oil, petrolatum preparations, talc, topical starch and zinc oxide. The skin protectants comprise 5–50% of the formulation applied to the topsheet and preferably 25–40%.

Skin protectants which are preferably utilized in the treatment compositions for preparing the topsheet of this invention are silicone and zinc oxide. Dimethicone, a silicone, is remarkably free of toxicity. It clings to the skin and repels water. It will effectively seal a wound or irritation against further frictional irritants. Dimethicone is safe and effective for use on the skins of people of all ages. It can be applied in generous amounts and as often as needed. The treatment preparations can contain as much as 50% dimethicone, preferably up to 30% and are entirely safe in these amounts.

Zinc oxide is a skin protectant conventionally used to protect skin from dryness and other harmful substances. It absorbs toxic substances and serves as a lubricant. It is extremely safe. It has cooling action, is slightly astringent, antiseptic, antibacterial and protective. Zinc oxide is preferably utilized in and amount of 1–25% but can safely be used in an amount of up to 40% of the total treatment composition.

Allantoin, another example of a suitable protectant as well as of a healing agent is a compound that is nontoxic, non-allergenic and nonirritating when applied to the skin. It has the ability to protect against moisture and the irritation of diaper rash. It is considered safe and effective for people of all ages when applied in concentration of 0.5–2.0%, and can be utilized as often as needed.

(2) Surfactants. Nonionic surfactants are utilized in the composition applied to the topsheet. Important examples of the nonionics, include the alkyl ethoxylates, the ethoxylated alkyl phenols, the fatty acid ethanol amides and complex polymers of ethylene oxide, propylene oxide and alcohol. Commonly used surfactants include polysorbate 20, polysorbate 85, sorbitan tristearate, sorbitan trioleate, glyceryl, glyceryl monostearate, glyceryl monooleate etc. Preferably the surfactant is employed in an amount of 10–30%.

(3) Humectants. Humectants are substances used to preserve the moisture content of materials and are conventionally used in compositions such as creams and lotions and can be included in the compositions used to treat the topsheet. The most widely used humectants are glycerin, propylene glycol and sorbitol. Glycerin is recognized as being highly inert and innocuous and may be applied generously. The recommended amount for use is a 20–45% concentration. The skin treated with glycerin stays moist and will not be irritated by other agents. In addition to its other functions in the treatment composition, propylene glycol serves as a humectant. Propylene glycol is characterized by its ability to permeate through the skin more readily than any another substance including glycerin and is also less expensive. The propylene glycol acts as a solvent and as a wetting agent as well as to absorb moisture.

(4) Healing Agents. There are no FDA approved healing active ingredients for use in treating and preventing primary irritation such as diaper dermatitis. This is due to the fact that such agents have not been subjected to controlled pharmacological studies. Specific known healing agents, such as specific anti-fungals, anti-biotics, corticosteroids, anti-inflammatories including nonsteroidals can be used herein for exerting their well known pharmacological capabilities. FDA conditionally approved agents include: cholecalciferol (vitamin D), cysteine HCl, live yeast cell derivatives, 1-isoleucine, 1-methionine, 1-phenylalanine, 1-tyrosine, racemethionone, and vitamin A and combinations of these such as vitamins A and D. Vitamin A and D can be introduced into these compositions as cod liver oil or shark liver oil or as the vitamin itself. The fish oils have healing and lubricating activity as well as functioning to protect the skin from urine and other irritants. These healing agents are utilized in an amount of 5–13 percent of the treatment composition.

(5) Anti-microbials. Antimicrobials useful in this invention and suitable for incorporation into the topsheet are intended to protect the skin from infection from body wastes. These agents reduce microbial growth and thus prevent or reduce microbial metabolic action on discharged urine and/or feces. The result is decreased ammonia concentration as well as that of other toxic metabolites of microbial action on these substrates. Highly preferred for use are the quaternary nitrogen based antimicrobials and the bis-biquanides. The antimicrobial agents which contain a single quaternary nitrogen moiety include the hydrocarbyl substituted ammonium compounds as well as those compounds wherein the quaternary nitrogen is part of a cyclic structure ring such as pyridium compounds. Representative examples of suitable quaternary nitrogen based antimicrobial agents include methylbenzethonium chloride, benzalkonium chloride, dodecyltrimethyl ammonium bromide, tetradecylmethyl ammonium bromide and hexadecyltrimethyl ammonium bromide. Cyclic quaternary nitrogen based antimicrobial agents include dodecylpyridiniun chloride, tetradecylpyridinium chloride, and tetradecyl-4-methylpyridinium. The most preferred bis-quanides include 1,6-bis(4-chlorophenyl)diquanidohexane, known as chlorhexidine and its water soluble salts. These two types of antimicrobial agents have a combination of desirable properties, e.g., relatively low toxicity and irritation potential and acceptable physical characteristics. FDA conditionally approved antimicrobials for use in treating and preventing diaper dermatitis are (a) Benzalkonium chloride (b) benzethonium chloride and (c). methylbenzethonium chloride.

6). Emollients. Emollients are substances used to impart a softness or resiliency to skin. An example of an emollient would be Miglyol 812 defined as a caprylic/capric triglyceride or a fractionated coconut oil or a medium chain triglyceride.

Treatment compositions comprised of propylene glycol, a surfactant and a protectant and preferably including an antimicrobial have been found to be safe and effective. Such compositions could also include an anti-odorant and a wound healer.

A preferred treatment compositions utilizes dimethicone as the skin protectant, n-alkyldimethylbenzyl ammonium chloride as a combined antimicrobial/surfactant in combination with propylene glycol. A particularly preferred treatment composition comprises 55% propylene glycol, 30% dimethicone and 15% n-alkyldimethylbenzyl amomonium chloride.

As previously noted the treatment compositions are entirely nonaqueous and are applied to the topsheet by spraying, impregnating, printing as with a Gravure press, and other conventional treatment methods utilizing an amount of 5–50 weight percent, preferably 5–25 weight percent and most preferably 10–20 weight percent treatment composition referenced to the topsheet.

The topsheet treatment, which, because it imparts a dry and smooth hand, has been found useful with conventional skin and toilet tissue applications, for use per se as cleansing tissues, facial tissues and the like.

The topsheet is adhered to the absorbent core and the absorbent core in turn to the impervious backsheet, in the conventional manner, utilizing adhesives preferably printed hot melt (adipic acid) or by application of heat and pressure or ultrasound welding.

Waste containment garments, pads, bandages and dressings prepared from the composite structures of the invention expediently transfer the protectants such as dimethicone to the skin of the user and thereby protect the skin from the subsequent exposure to body wastes, and toxic substances contained therein. They also effectively prevent the metabolic end products of microbial metabolism from acting as irritants and toxic substances.

Still further they provide friction reducing qualities which result in the prevention or onset of bed sores and the like. The use of such devices containing the treated topsheet virtually eliminates the need for using medicated creams, ointments or powders.

In laboratory testing of such prepared waste containment garments, carried out by the applicant or under his supervision, the reduction of the coefficient of friction could be demonstrated.

The treatment solutions are prepared by simple thorough admixing of the components in a mixing container and mixing continuously to obtain a uniform treatment composition. The mixing can be carried out in a propeller mixer or a homogenizer or by employing other conventional equipment and procedures. As previously noted the conventional means of application are used, spraying, printing, impregnating, etc. in applying the treatment compositions to the topsheet.

The following examples of formulations for treatment of topsheets are given to more fully illustrate the invention but are not to be construed in limitation thereof.

Treatment compositions were prepared by simple and thorough mixing of the ingredients as listed below:

EXAMPLE 1

A commercially available diaper topsheet constituting a 15 gram per yard square spun bond polypropylene was treated with a composition as described below. The treatment was applied by means of a Gravure print roll such that 18 weight percent referred to the untreated topsheet was added.

Treatment composition for Example 1 and 11.

| Agent | Per Cent |
| --- | --- |
| Propylene glycol USP | 60.00 |
| Silicone SF 18-350 | 30.00 |
| N-alkyldimethylbenzyl | 10.00 |
| ammonium chloride | 100.00 |

A commercially available diaper topsheet described as a 15 gram per yard square spun bond polypropylene was treated with a composition as described above. The treatment was applied by means of a Gravure print roll such that 6 weight percent referred to the untreated topsheet was added.

Samples of treated topsheets as described in Example 1 and 11 were evaluated for transfer of the non-water soluble dimethicone by physical contact with the skin of a user participant. All participants reported perceptible levels of dimethicone on their skin after use. The participants who were provided with control samples reported no such transfer.

In order to evaluate the functionality of the treated topsheet of Examples 1 and 11, two tests were carried out. This first test called a "strike through" test consists of pouring 50 ml of saline solution onto pretreated topsheets prepared as set out in Examples 1 and 11, and measuring the time required for passage of the saline through to a filter paper core.

Results are as follows:

| Control | 3.6 seconds |
| --- | --- |
| 6% treated | 4.3 seconds |
| 18% treated | 3.6 seconds |

The results establish that treatment did not affect strike through.

The second test which was carried out is the "wet back" test and measures the amount in grams of saline allowed to pass back through a topsheet after wetting.

The results are as follows:

| | |
|---|---|
| Control | 0.19 grams |
| 6% treated | 0.15 grams |
| 18% treated | 0.87 grams |

It was concluded that the treatment at 18% showed an increase in wet back, but not enough to cause a failure which is normally judged to occur at 2.0 grams, or higher.

EXAMPLE 111

A commercially available diaper topsheet described as an 18 gram per yard square thermally bonded polypropylene was treated with a composition as described below.

The treatment composition was applied to the topsheet by means of a Gravure print roll such that levels of 10 and 15 weight percent referred to the untreated topsheet were added.

Treatment composition of Example 111:

| Agent | % W/W |
|---|---|
| Propylene glycol USP | 55.00 |
| Dimethicone SF-18-350 | 30.00 |
| N-Alkyl Dimethylbenzyl ammonium Chloride | 15.00 |
| | 100.00 |

Samples of both the 10 and 15% treated topsheets were evaluated for transfer of dimethicone to human skin by tactile means. All participants noted a transfer versus an untreated control used as a comparison.

As in Examples 1 and 11, objective tests for "strike through" and "wet back" were carried out, but this time using a full diaper, not filter paper as the core as in Example 1 and 11.

The results are as follows:

| | Strike Through (seconds) | Wet Back (grams) |
|---|---|---|
| Control | 2.7 | 0.15 |
| 10% treatment | 3.2 | 0.25 |
| 15% treatment | 3.2 | 0.15 |

It was concluded that while the non-water soluble dimethicone transfers to the skin by contact, the treatment composition does not interfere with passage of liquid into the core.

EXAMPLES 1V, V and V1.

A commercially available diaper topsheet described as a 15 gram per yard square spun bond polypropylene was treated using the composition described below. The treatment composition was applied by means of a Gravure point roll such that 10 weight percent referred to the untreated topsheet was added.

EXAMPLE 1V

| Agent | % W/W |
|---|---|
| Propylene glycol USP | 50.00 |
| Dimethicone USP | 35.00 |
| Methylbenzethonium chloride | 0.1 |
| N-alkyldimethylbenzyl ammonium chloride | 14.9 |
| | 100% |

EXAMPLE V

| Agent | % W/W |
|---|---|
| Propylene glycol USP | 65.00 |
| Dimethicone USP | 20.00 |
| N-alkyldimethylbenzyl ammonium chloride | 13.00 |
| Allantoin | 2.00 |
| | 100.00% |

EXAMPLE V1

| Agent | % W/W |
|---|---|
| Propylene glycol USP | 75.00 |
| Zinc oxide | 20.00 |
| N-alkyldimethylbenzyl ammonium chloride | 5.00 |
| | 100.00% |

Evaluation of the samples showed the same tactile results as noted in Example 1, 11, and 111.

The samples of Example 1V, V and V1 functioned as described for Examples 1, 11 and 111.

EXAMPLE V11

A commercially available incontinent bed pad topsheet described as a 15 gram per yard square spun bond polypropylene was treated with a treatment solution as set out below. The treatment solution was applied by an aerosol spray such that 18–20 weight percent referred to the untreated topsheet was added.

| Agent | % W/W |
|---|---|
| Dimethicone SF 18-350 | 40.00 |
| Miglyol 812 | 37.00 |
| Brij 93 | 7.50 |
| Tween 85 | 7.50 |
| Propylene glycol | 6.00 |
| Dowicil 200 | 2.00 |
| | 100.00 |

The treated topsheet was added to a commercially available incontinent bed pad and adhered to the underlying layers using a hot melt adhesive.

The treated pad was used by a number of subjects, all of whom reported an ease of use due to less friction between the user and the pad.

Additional tests were performed using saline to mimic urine to evaluate "strike through" and "wet back". In each incident, the performance of the treated topsheet was equal to that of the untreated control.

I claim:

1. A liquid pervious thin film or fabric sheet formed of synthetic and/or natural materials which has been treated with a substantially non-aqueous composition comprising propylene glycol, at least one non-water soluble skin protectant and at least one surfactant.

2. The liquid pervious thin film or fabric sheet according to claim 1 wherein said propylene glycol is present in an amount of 5–75% of said composition.

3. The liquid pervious thin film or fabric sheet according to claim 1 wherein said propylene glycol is present in an amount of 10–55% of said composition.

4. The liquid pervious thin film or fabric sheet according to claim 1 wherein said non-water soluble skin protectant is present in an amount of 5–50% of said composition.

5. The liquid pervious thin film or fabric sheet according to claim 1 wherein said skin protectant is present in an amount of 20–40% of said composition.

6. The liquid pervious thin film or fabric sheet according to claim 1 wherein said surfactant is present in an amount of 0.5–30% of said composition.

7. The liquid pervious thin film or fabric sheet formed according to claim 1 wherein said surfactant is present in an amount of 10–30% of said composition.

8. The liquid pervious thin film or fabric sheet according to claim 1 wherein said composition has been applied to said sheet in an amount of 5–50 weight % referred to said sheet.

9. The liquid pervious thin film or fabric sheet according to claim 1 wherein said composition has been applied to said sheet in an amount of 5–25 weight % referred to said sheet.

10. The liquid pervious thin film or fabric sheet according to claim 1 wherein said composition has been applied to said sheet in an amount of 10–20 weight % referred to said sheet.

11. The liquid pervious thin film or fabric sheet according to claim 1 wherein said composition at least one member selected from the group consisting of emollients, antimicrobials, odor reducing agents, humectants and healing agents.

12. The liquid pervious thin film or fabric sheet according to claim 1 Therein said sheet is made of a member selected from the group consisting of polyesters, polyolefins, polyacrylonitriles, cellulose and mixtures thereof.

13. A liquid pervious thin film or fabric sheet formed of synthetic and/or natural materials which has been treated with a substantially non-aqueous composition comprising 55% propylene glycol, 30% dimethicone and 15% N-alkyl dimethylbenzyl ammonium chloride.

14. A liquid pervious thin film or fabric sheet formed of synthetic and/or natural materials which has been treated with a substantially non-aqueous composition comprising 60% propylene glycol, 30% dimethicone and 10% N-alkyl dimethylbenzyl ammonium chloride.

15. The disposable absorbent article suitable for absorbing discharged body waste characterized by substantial moisture absorptive capacity and an ability to prevent contact irritant dermatitis and the occurrence of bed sores and ulcerations comprising (a) a liquid pervious topsheet as claimed in claim 1 (b) a fluid impervious backing sheet and (c) a hydrophillic absorbent core positioned between said backing sheet and said topsheet.

16. The disposable article of claim 15 wherein said topsheet is substantially porous and permits liquids to readily pass through into said underlying core, said topsheet is made of a member selected from the group consisting of polyesters, polyolefins, polyacrylonitriles, cellulose and mixtures thereof, wherein said article absorbs discharged body waste while also preventing contact dermatitis and the occurrence of bed sores and ulcerations by reducing frictional wear on the skin of the user as said topsheet in use transfers to the exposed skin in contact with said disposable article said non-water soluble skin protectant.

17. The disposable absorbent article of claim 15 wherein said absorbent core comprises a batt or web of hydrophillic fibrous material.

18. The disposable absorbent article of claim 17 wherein said core comprises a batt or web of at least one member selected the group of cellulose, modified cellulose, rayon and polyesters.

19. The disposable article of claim 15 wherein said backing sheet comprises at least one member selected from the group consisting of polyethylene and polypropylene.

20. A diaper or incontinent brief prepared from the disposable absorbent article of claim 15.

21. An incontinent bed sheet or pad prepared from the disposable article of claim 15.

22. A wound dressing prepared from the disposable absorbent article of claim 15.

* * * * *